US007098367B2

(12) United States Patent
Ledford et al.

(10) Patent No.: US 7,098,367 B2
(45) Date of Patent: Aug. 29, 2006

(54) PROCESS FOR THE PREPARATION OF ALKYLENE GLYCOLS

(75) Inventors: John S. Ledford, Richmond, TX (US); Jaap W. Van Hal, Fresno, TX (US); Xiankuan Zhang, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 36 days.

(21) Appl. No.: 10/923,961

(22) Filed: Aug. 23, 2004

(65) Prior Publication Data

US 2006/0041173 A1    Feb. 23, 2006

(51) Int. Cl.
*C07C 31/20*    (2006.01)
*C07C 31/18*    (2006.01)
(52) U.S. Cl. ...................................... 568/867; 568/680
(58) Field of Classification Search ................ 568/867, 568/680
See application file for complete search history.

(56) References Cited

U.S. PATENT DOCUMENTS

| 4,243,759 A | | 1/1981 | Haas |
| 4,307,256 A | * | 12/1981 | Cipriani et al. ............. 568/867 |
| 4,393,254 A | * | 7/1983 | Johnson et al. ............. 568/867 |
| 4,521,548 A | | 6/1985 | Christen et al. |
| 6,137,015 A | * | 10/2000 | Strickler et al. ............ 568/867 |

OTHER PUBLICATIONS

John H. Biel; Antihistaminics. I. Some Ethylene Diamines and an Aminoether; J. Am. Chem. Soc., vol. 71, issue 4, p. 1306-1309 (Apr. 1949).

* cited by examiner

*Primary Examiner*—Elvis O. Price
(74) *Attorney, Agent, or Firm*—Jim D. Wheelington

(57) ABSTRACT

Disclosed is a process for the preparation of alkylene glycols from the corresponding alkylene oxide, such as ethylene glycol from ethylene oxide, in the presence of water, a catalyst and, optionally, carbon dioxide. The catalyst contains amines which are weak bases, specifically having $pK_a$ of at least 5.5, preferably 8 to 11. The amines may be primary, secondary, tertiary or a blend thereof or may be a compound having a structural combination of primary, secondary and/or tertiary amines.

19 Claims, 2 Drawing Sheets

PROCESS FOR THE PREPARATION OF ALKYLENE GLYCOLS

BACKGROUND OF THE INVENTION

1. Field of the Invention

This invention relates to a process for the preparation of alkylene glycols from the corresponding alkylene oxide in the presence of water and a catalyst. A specific example of the process is in the preparation of ethylene glycol from ethylene oxide.

2. Description of the Prior Art

The production of alkylene glycols from alkylene oxides is known and is practiced commercially. Of particular interest is the production of ethylene glycol from ethylene oxide. The thermal hydration of ethylene oxide in water produces monoethylene glycol (MEG), a major active component in antifreeze. MEG can also be used as a base material in the production of polyester fibers, resins, films and bottles.

Hydration of ethylene oxide can be through catalytic and non-catalytic means. Non-catalytic hydration of ethylene oxide to MEG requires a large excess of water to inhibit the formation of diethylene glycol (DEG) and other higher glycols. Even with a large excess of water the molar selectivity to MEG is only about 90%. In addition, the water must be distilled from the glycol to obtain a high purity product.

Catalytic hydration of ethylene oxide may use smaller amounts of water and is carried out at lower temperatures. There are numerous examples of catalysts for hydration of an alkylene oxide to alkylene glycol.

U.S. Pat. No. 4,551,566 discloses a process for the production of alkylene glycols by the hydration of alkylene oxides in the presence of a water soluble vanadate salt in a liquid medium having a pH between 5 and 12. The adjustment of the pH to this range by addition of acids or bases affects rate and selectivity of the reaction.

U.S. Pat. No. 6,316,571 discloses preparation of alkylene glycols by reacting alkylene oxide with water in the presence of a polycarboxylic acid derivative, such as salts of malonic acid, succinic acid, tartaric acid, maleic acid, adipic acid, terephthalic acid, citric acid, trimetallitic acid and pyromellitic acid, immobilized on a resin support.

U.S. Pat. No. 4,760,200 discloses a process for liquid phase hydration of alkylene oxides to the corresponding alkylene glycols in a medium containing a water miscible alkylene glycol ether cosolvent. The process may or may not use a catalyst but if a catalyst is used it may be a metallate anion, such as a vanadate or tungstate anion, in association with electropositive complexing moieties, such as tertiary amines, on a solid substrate.

U.S. Pat. No. 6,147,265 discloses a process for producing alkylene glycol from alkylene oxide with a catalyst of an anion-exchange resin with a substrate of a vinyl aromatic compound polymer and a quaternary ammonium group, such as tertiary amine, bonded to aromatic groups of the polymer via a connecting group of a chain length of three or more atoms.

U.S. Pat. No. 5,488,184 discloses a process for preparation of alkylene glycols from alkylene oxides and water in the presence of a catalyst of a solid material having electropositive sites, such as anionic exchange resins containing tertiary amines, coordinated with non-metalate and non-halogen anions. The tertiary amines may be linked to the matrix of the solid material by a benzyl group. When a quarternary ammonium type of anionic exchange resin with a bicarbonate anion, the presence of carbon dioxide is detrimental to the performance of the catalyst.

U.S. Pat. No. 3,629,343 discloses a process for the production of alkylene glycols by catalytic hydration of alkylene oxides in the presence of carbon dioxide and an ammonium halide catalyst which may be formed in situ, e.g., triethylamine and ethyl iodide to form tetraethylammonium iodide.

U.S. Pat. No. 4,937,393 discloses a method for preparing ethylene glycol or propylene glycol with a catalyst of a carboxylic acid and a carboxylic acid salt which may be a salt of a basic-nitrogen containing compound, such as an aliphatic primary secondary or tertiary amine or a cycloaliphatic primary, secondary or tertiary amine. It is preferable that the hydration reaction proceeds in the absence of carbon dioxide.

U.S. Pat. No. 4,393,254 discloses a process for the production of alkylene glycols by catalytic hydration of alkylene oxides in the presence of a heterogeneous, partially amine-neutralized sulfonic acid catalyst which are sulfonic acid-type ion exchange resins, such as a styrene-divinylbenzene copolymer matrix with pendant sulfonic acid groups, modified by passing amine through the resin to partially neutralize the sulfonic acid groups. Primary, secondary or tertiary amines may be used but tertiary amines are preferred.

U.S. Pat. No. 4,307,256 discloses a process for the preparation of alkylene glycols from the corresponding alkylene oxides in the presence of water, carbon dioxide and an organic base, such as a tertiary amine, specifically triethylamine, dimethylaniline and pyridine.

SUMMARY OF THE INVENTION

This invention concerns preparation of alkylene glycols from the corresponding alkylene oxides in the presence of water and a catalyst containing amines which are weak bases, specifically having pKa of at least 5.5, preferably 8 to 11. The amines may be primary, secondary, tertiary, a blend of primary, secondary and/or tertiary amines or a structural combination of primary, secondary and/or tertiary amines. Carbon dioxide may also be present during the reaction or used to pretreat the catalyst.

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

Alkylene glycols can be obtained by reacting the corresponding alkylene oxide with water in the presence of a catalyst. Carbon dioxide may be added to the reaction medium to improve selectivity to the glycol.

Alkylene oxides are generally of the formula $R^1R^2(COC)R^3R^4$, where each $R^1$, $R^2$, $R^3$ and $R^4$ is independently hydrogen or an alkyl of from 1 to 10 carbon atoms. Examples of alkylene oxides are ethylene oxide, propylene oxide and butylene oxide. The corresponding alkylene glycol is generally of the formula $R^1R^2(COHCOH)R^3R^4$, where $R^1$, $R^2$, $R^3$ and $R^4$ are as defined above, and may be obtained by hydration of the alkylene oxide, i.e., reacting it with water to introduce a hydroxyl group and hydrogenate the oxygen. A mixture of glycols is formed (monoalkylene glycol, dialkylene glycol and higher alkylene glycols).

Figure 1:
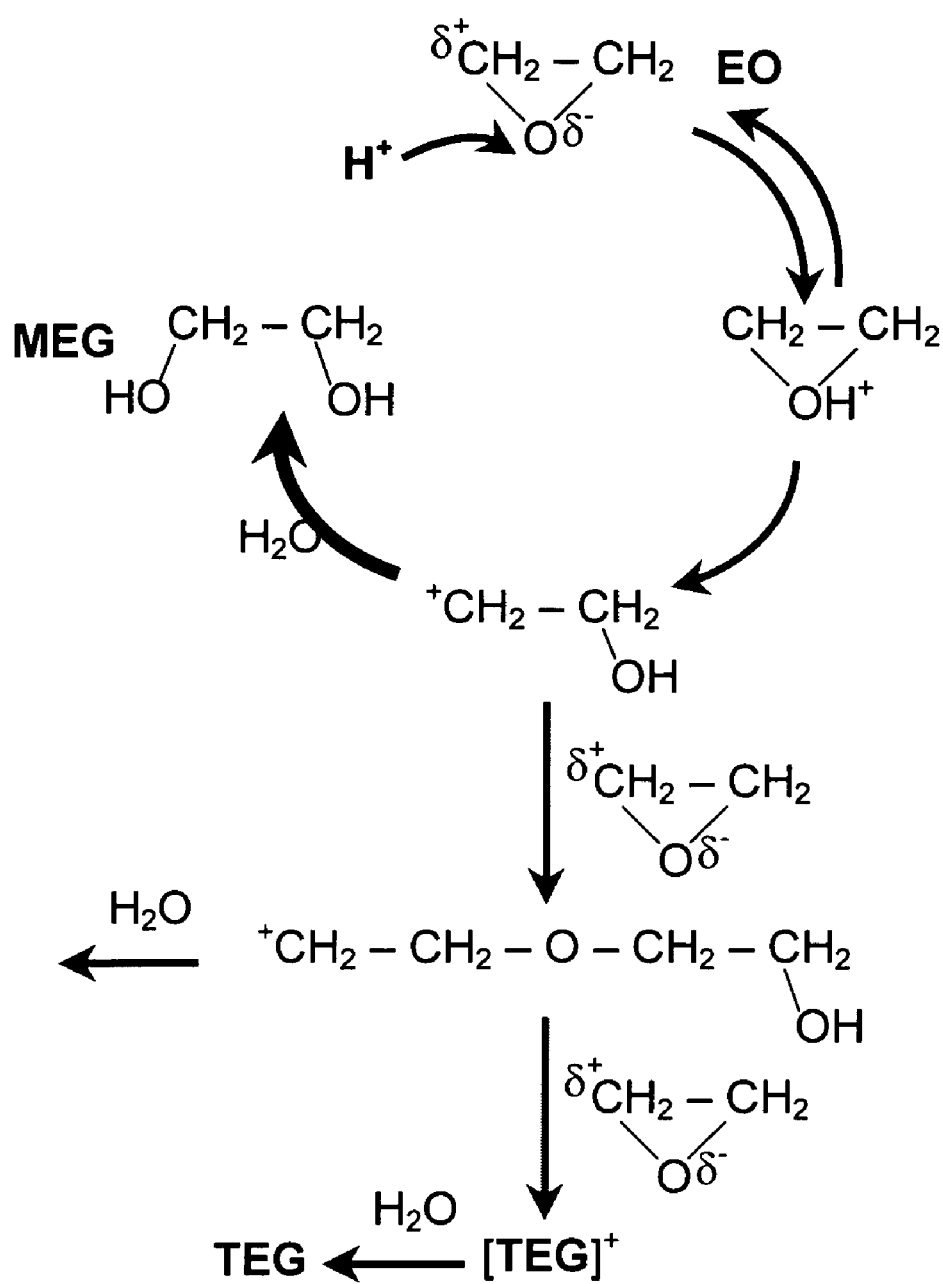
FIG. 1 is a proposed mechanism for an acid catalyzed reaction ethylene oxide to monoethylene glycol, diethylene glycol and triethylene glycol.
Figure 2:
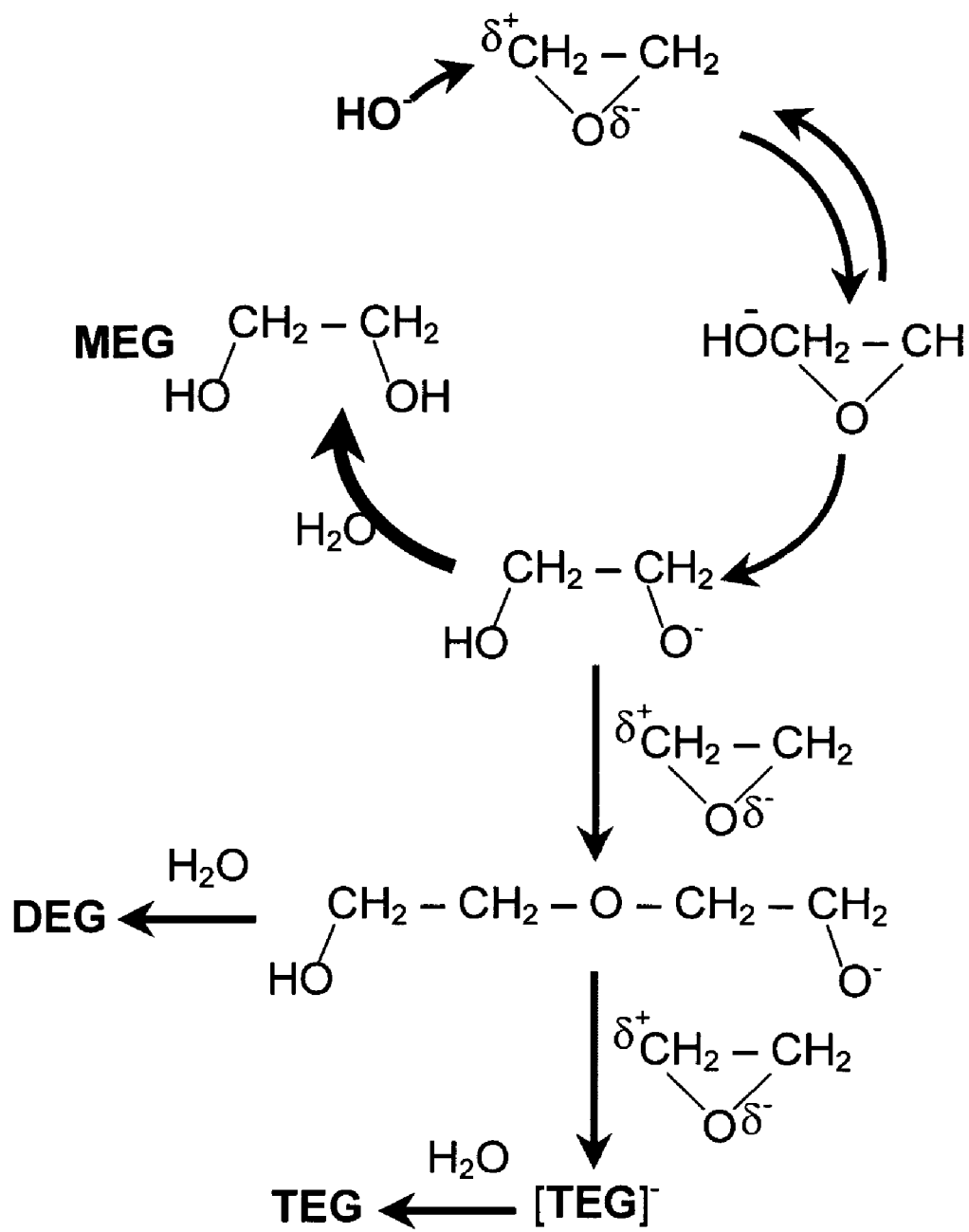
FIG. 2 is a proposed mechanism for a base catalyzed reaction ethylene oxide to monoethylene glycol, diethylene glycol and triethylene glycol.

Though the reaction of alkylene oxide and water to alkylene glycol proceeds non-catalytically, improvements in reaction rate, selectivity and reduced water can be realized by the use of catalysts. The catalyst may be acids or bases. Without intending to limit the scope of the invention as represented by the claims, it is believed that the reaction mechanism for hydration of alkylene oxides, such as ethylene oxide, to alkylene glycols, such as ethylene glycol, with an acid catalyst, i.e., having a pH less than 7, is different from that for a base catalyst, i.e., having a pH greater than 7. As shown in FIG. 1, it is believed that in a acid catalyzed reaction, an intermediate $CH_2^+CH_2OH$ is formed which is very reactive with ethylene oxide to form higher glycols, i.e., diethylene glycol (DEG) and triethylene glycol (TEG) rather than the more desirable monoethylene glycol (MEG). As shown in FIG. 2, it is believed that in a base catalyzed reaction, an intermediate $CH_2OHCH_2O—$ is formed which is less reactive with ethylene oxide. Of equal or greater importance, the acidity, basicity and other variables of the catalyst and/or reaction media can affect the kinetics of the reaction and the relative reaction rates of MEG, DEG and TEG.

While activity of a catalyst is a useful property in the conversion of an alkylene oxide to an alkylene glycol, of at least equal importance is the selectivity to a desired product. To increase the selectivity to monoalkylene glycol, the secondary reaction between the monoalkylene glycol and the alkylene oxide should be suppressed. Increasing the relative amount of water present in the reaction mixture suppresses the secondary reaction. However, large amounts of water subsequently have to be removed to recover the product.

As noted above, in the process of hydration of ethylene oxide to ethylene glycol MEG is a desirable product whereas production of DEG and TEG is to be minimized. As shown in FIGS. 1 and 2, an acid catalyst may be more advantageous than a base catalyst for producing MEG over DEG and TEG.

The catalysts of the present invention are primary or secondary amines of the formula:

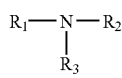

wherein $R_1$, $R_2$ and $R_3$ are hydrogen, alkyl, aryl or cycloalkyl radicals and are the same or different or are compounds containing moieties of two or more primary, secondary and/or tertiary amines of the formulae:

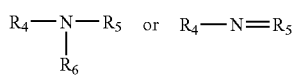

wherein $R_4$, $R_5$ and $R_6$ are hydrogen, alkyl, aryl or cycloalkyl radicals and are the same or different and R4 and R5 may form a fused ring. The catalysts of the present invention may be a mixture or blend of these amines, i.e., the catalysts may contain two or more primary, secondary and/or tertiary amines. The catalysts of the present invention may contain moieties of primary, secondary and/or tertiary amines as part of a chemical composition or structure.

An example of a simple primary amine is ethylamine. An example of a simple secondary amine is diethylamine. Examples of a cyclic secondary amine are hexamethyleneimine, 1,4,7,10-tetraazacyclododecane (Cyclen) and 3-(1-piperazine). An example of a simple tertiary amine is triethylamine. An example of a cyclic amine having two tertiary amino groups is 1,4-diazabicyclo[2,2,2]octane (DABCO). An example of a tertiary amine where R is an aryl is dimethylaniline. An example of an aromatic heterocyclic amine having a single tertiary amine is pyridine. Examples of a compound in which there are two or more moieties of primary, secondary and/or tertiary amines as part of the chemical composition or structure are ethylenediamine, 1,3-diaminopropane (DAP), 3,3'-diamino-N-methyl-dipropylamine, 1,5,8,12-tetraazadodecane, poly(ethylene amine), 5-benzimidazolecarboxylic acid, 2-dimethylaminopyridine (2-DMAP), 1,8-diazabicyclo[5,4,0]undec-7-ene (DBU), 1,5-diazabycyclo[4,3,0]non-5-ene (DBN) and N,N,N'N'-tetramethylethylenediamine (TMEDA).

The negative logarithm of the forward reaction equilibrium constant, $pK_a$, is related to the acid strength of a compound. The smaller the $pK_a$, the stronger the acid. The larger the $pK_a$ of the conjugate acid, the stronger is the base. The value of the $pK_a$ may be measured experimentally, taken from references or estimated from compounds of similar structure. The catalysts of the present invention have pKa of at least 5.5, preferably 8-11 and are weakly to moderately basic.

The catalyst of the present invention may be used as an unsupported catalyst or a supported catalyst. Examples of supports are metal oxides, such as silica, alumina, niobia, titania, zirconia or mixtures thereof, and resins, polymers carbons, zeolites or clays. The catalyst may be affixed to the support by methods known in the art. The catalyst is not limited by shape, size or particle distribution and may be formed as appropriate. Examples are powder, granules, spheres, cylinders, saddles, etc.

The invention having been generally described, the following examples are given as particular embodiments of the invention and to demonstrate the practice and advantages thereof. It is understood that the examples are given by way of illustration and are not intended to limit the specification or the claims to follow in any manner.

Experimental

Ethylene oxide (99.5%) was purchased from Specialty Gas Company, Houston, Tex. and used as received. Deionized water with Diglyme added as an internal standard (~2% w/w) was used for dilution of the ethylene oxide under nitrogen pressure. The mixture of EO/water was then shaken or stirred by magnetic agitation to assure a uniform mixture.

Catalysts for testing in the MultiClave™ that has 10 reactor tubes with glass liners inside were weighed out before the reaction in the glass liners and then dissolved in or diluted with deionized water. The liners were filled not more than halfway with catalyst at any time. The weights of the liners and the catalyst were recorded and the liners placed in the MultiClave™ reactor tubes. One reactor cell did not have any catalyst and was filled with 10 ml of deionized water as a control (thermal hydration, see below). The first reactor had a thermocouple inserted in place of the feed line to estimate the internal temperature of the other reactors. The system was then closed and the reactor purged at least three times with nitrogen The nitrogen pressure was reduced to about 30 psig. Carbon dioxide could also be introduced into the system as this point, if desired. The catalyst was then agitated by Teflon™ coated magnetic stir bars and the internal temperature raised to about 100° C. A pump for the EO/water mixture was run at 5 ml/min until the feed lines were flushed out. A 12-port valve was then used to advance the flow of the EO/water to each of the nine reactor cells for exactly two minutes as controlled by an external programmable timer. In this manner, about 10 ml of the EO/water mixture was delivered to the nine available reactor cells. The system was then pressurized to about 250 psig using either nitrogen or carbon dioxide. The reactor cells were maintained at 100° C. for 10 hours before being cooled to room temperature.

The amines for catalyst testing were procured either directly from the manufacturer or from chemical material suppliers or were prepared by published preparations in the glass liners and used without further purification. Some catalysts were pretreated with carbon dioxide in situ to try to prepare ammonium carbonate complexes from amine functional groups.

Thermal Hydration Control

A thermal hydration control was run internally in each set of reactions conducted using the MultiClave™ system. The reaction was run by adding 2 ml deionized water to one of the reactor glass liners and at the same conditions as for Example 1 below. The average selectivity for thermal hydration under these conditions was about 84%.

All the analysis by G.C. was performed on a Varian 3900 single channel GC equipped with an FID. Selectivity was calculated based on the amount of MEG, DEG and TEG detected, corrected for the molar amounts of EO necessary to form each product.

EXAMPLE 1

Ethylenediamine (EDA)

Ethylene diamine (EDA, Aldrich 99%). The EDA (0.5 g) was added to 2 ml of deionized water in a 15 ml glass liner. The liner was placed in an Autoclave Engineers Multi-Clave™ 10X system, purged three times with 250 psig of carbon dioxide gas (Matheson, Coleman) for one hours. The carbon dioxide pressure was then reduced to about 50 psig. The reactor was then heated to 100° C. over about one hour. Once the temperature had stabilized, a 10 ml sample of EO:water (4:1 w/w) with diglyme (Aldrich) added at about 1% w/w concentration as an internal standard. The mixture was pressurized to 250 psig with carbon dioxide and magnetically agitated at 100° C. for 10 hours. The resulting solution was clear and light yellow. The sample was analyzed by G.C. to give a selectivity of 92% relative to the thermal hydration control sample of 83% at similar dilution.

EXAMPLE 2

Diethylamine (DEA)

Diethyl amine (DEA, Aldrich, 99.5%, 0.20 g) was dissolved in 5 ml of water and treated as above. The product was clear with little if any color to the solution. The selectivity to MEG was 93%, compared to the thermal hydration control (5 ml of water) at 90%.

EXAMPLE 3

Hexamethyleneimine

Hexamethyleneimine (Acros, 99%) The hexamethyleneimine (0.19 g) was dissolved in 2 ml of deionized water and treated as in Example 1. The product was dark yellow in color. The selectivity was 93% to MEG, compared to the thermal hydration control of 84%.

EXAMPLE 4

1,4,7,10-tetraazacyclododecane (Cyclen)

Cyclen (1,4,7,10-tetraazacyclododecane, Aldrich 99%). The Cyclen (0.2 g) was dissolved in 5 ml of deionized water and treated as in Example 1. The product had a light yellow tint. The selectivity to MEG was 92% compared to a thermal hydration control of 89%.

EXAMPLE 5

1,4-diazabicyclo[2,2,2]octane (DABCO)

DABCO (1,4-Diazabicyclo[2,2,2]octane, Aldrich, 99.5%). The DABCO (0.23 g) was dissolved in 5 ml of deionized water and treated as Example 1. The product obtained was clear and colorless and the selectivity to MEG was 96%, compared to the thermal hydration control at 90%.

EXAMPLE 6

1,3-diaminopropane (DAP)

1,3 Diaminopropane (DAP, Aldrich 99.5%). The DAP was dissolved in 2 ml of deionized water and treated as Example 1. The product obtained was light yellow and assumed to contain polymerized product. The selectivity of the remaining product was 95% for MEG, compared to a thermal hydration control of 84%.

EXAMPLE 7

3,3'-diamino-N-methyldipropylamine 3,3'-diamino-N-methyldipropylamine (Aldrich, 96%). The amine (0.3 g) was dissolved in 5 ml of deionized water and treated as Example 1. The product was clear and yellow in color with the selectivity to MEG estimated at 94% compared to a thermal hydration control of 88%.

EXAMPLE 8

1,5,8,12-tetroazadodecane 1,5,8,12-tetraazododecane (Strem, 98%). The amine (0.19 g) was dissolved in 2 ml of deionized water and treated as Example 1. The product was faint yellow with selectivity to MEG of 93% compared to the thermal hydration control at 84%.

EXAMPLE 9

Poly(ethylene amine)

Poly(ethylene)imine (Mn=423, Aldrich). The polymer (0.34 g) was dissolved in 2 ml deionized water and treated as Example 1. The product was faint yellow with a selectivity to MEG of 93%, compared to the control at 84%.

EXAMPLE 10

2-dimethylaminopyridine (2-DMAP)

Catalytic hydration using 2-dimethylaminopyridine (2-DMAP, Aldrich, 97%). The 2-DMAP (0.24 g) was mixed with 5 ml of deionized water and treated as Example 1. The product was clear and faint yellow in color with a selectivity to MEG of 92% compared to the thermal hydration control at 81%.

EXAMPLE 11

1,5-diazabycyclo[4,3,0]non-5-ene (DBN)

Catalytic hydration using 1,5-diazobicyclo[4,3,0]nonene (DBN, Aldrich, 98%). The DBN (0.32 g) was mixed with 5 ml of deionized water and treated as Example 1. The resulting product was light yellow in color with a selectivity to MEG of 92% compared to 88% for the thermal hydration control.

EXAMPLE 12

Tetramethylethylenediamine (TMEDA)

Catalytic hydration using N,N,N',N'-tetramethylethylenediamine (TMEDA, Aldrich, 99%) The TMEDA (0.28 g) was dissolved in 5 ml of deionized water and treated as Example 1. The resulting product was light yellow in color with a selectivity to MEG of 95%, compared to the thermal hydration control of 88%.

Comparative Example 1

Dimethylaniline

N,N'-Dimethylaniline (Aldrich, 99.5%). The N,N'-dimethylaniline (0.3 g) was suspended in 5 ml water and treated as in Example 1. The product was light yellow in color. The selectivity to MEG was 88% compared to a thermal hydration control at 88%.

Comparative Example 2

Pyridine

The pyridine (0.074 g) was dissolved in 2 ml of water and treated as above. The product was dark brown with a brown film of solid on top. The selectivity to MEG was 86% with the thermal hydration control of 83% at similar dilution with significant amounts of decomposition products from the pyridine observed in the GC baseline.

Comparative Example 3

N-(1-adamantyl)urea

Catalytic hydration using N-(1-adamantyl)urea. The N-(1-adamantyl)urea (0.64 g) was suspended in 5 ml of deionized water and treated as Example 1. The product was cloudy with a selectivity to MEG of 90%, compared to the thermal hydration control of 88%

Comparative Example 4

1,10-phenathroline (PHEN)

Catalytic hydration using 1,10-phenatroline (PHEN, Strem). The PHEN (0.35 g) was dissolved in 5 ml of deionized Water and treated as Example 1. The resulting product was light brown in color with a selectivity to MEG of 90% compared to 89% for the thermal hydration control.

Comparative Example 5

Thermal Hydration

Thermal hydration (dilute). The reaction was run by adding 5 ml of deionized water to the reactor's glass liner and treating the reaction as Example 1. The average selectivity for the thermal hydration control was about 88%.

| Example | pK$_a$ | Selectivity |
|---|---|---|
| 1: ethylenediamine (EDA) | 9.95 | 92 |
| 2: diethylamine (DEA) | 10.8 | 90 |
| 3: hexamethyleneimine | 10 | 93 |
| 4: 1,4,7,10-tetraaza cyclododecane (Cyclen) | 11–13* | 92 |
| 5: 1,4-diaza bicyclo[2,2,2]octane (DABCO) | 8.82 | 96 |
| 6: 1,3-diaminopropane (DAP) | 10.65 | 96 |
| 7: 3,3'-diamino-N-methyldipropylamine | 10 | 94 |
| 8  1,5,8,12-tetraazadodecane | 11 | 93 |
| 9: poly(ethylene amine) | 11 | 93 |
| 10: 2-dimethyl aminopyridine (2-DMAP) | 9.2 | 92 |
| 11: 1,5-diazabycyclo[4,3,0] non-5-ene (DBN) | 11–13* | 92 |
| 12: tetramethyl ethylenediamine (TMEDA) | 10.72 | 95 |
| Comparative 1: Dimethylaniline | 5.07 | 88 |
| Comparative 2: pyridine | 5 | 87 |
| Comparative 3: N-(1-adamantyl)urea | 0.18 | 90 |
| Comparative 4: 1,10-phenathroline (PHEN) | 4.27 | 90 |
| Comparative 5: Thermal hydration | 5 | 88 |

*Estimated

As shown by the data above, the catalyst not only have an amine structure but must also have a pK$_a$ of at least 5.5.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for the preparation of alkylene glycols comprising reacting an alkylene oxide with water in the presence of a catalyst of:
   a) a primary or secondary amine of the formula:

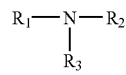

wherein $R_1$, $R_2$ and $R_3$ are hydrogen, alkyl, aryl or cycloalkyl radicals and are the same or different or
   b) containing moieties of two or more primary, secondary or tertiary amines of the formulae:

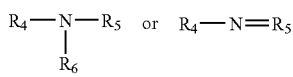

wherein $R_4$, $R_5$ and $R_6$ are hydrogen, alkyl, aryl or cycloalkyl radicals and are the same or different and $R_4$ and $R_5$ may form a fused ring;

said catalyst having a $pK_a$ of at least 5.5.

2. The process of claim 1 wherein the $pK_a$ is in the range of from 8 to 11.

3. The process of claim 1 additionally comprising reacting alkylene oxide in the presence of carbon dioxide.

4. The process of claim 1 additionally comprising pretreating the catalyst with carbon dioxide.

5. The process of claim 1 wherein the alkylene oxides are of the formula $R^1R^2(COC)R^3R^4$, where each $R^1$, $R^2$, $R^3$ and $R^4$ is independently hydrogen or an alkyl of from 1 to 10 carbon atoms and the alkylene glycol is of the formula $R^1R^2(COHCOH)R^3R^4$.

6. The process of claim 2 wherein the alkylene oxides are ethylene oxide, propylene oxide or butylene oxide.

7. The process of claim 1 wherein the alkylene oxide is ethylene oxide and the alkylene glycol is ethylene glycol.

8. The process of claim 1 wherein the process is carried out at a temperature from about 20° C. to 250° C.

9. The process of claim 8 wherein the temperature is 50° C. to 200° C.

10. The process of claim 1 wherein the process is carried out at a pressure greater than atmospheric.

11. The process of claim 10 wherein the pressure is 25 psig to 1000 psig.

12. The process of claim 1 wherein the molar ratio of alkylene oxide to water is in the range from about 5 to 25.

13. The process of claim 1 wherein the catalyst is a mixture or blend of two or more primary, secondary and/or tertiary amines.

14. The process of claim 1 wherein the catalysts contains moieties of primary, secondary and/or tertiary amines as part of its chemical composition or structure.

15. The process of claim 1 wherein the catalyst is ethylamine.

16. The process of claim 1 wherein the catalyst is diethylamine.

17. The process of claim 1 wherein the catalyst is hexamethyleneimine, 1,4,7,10-tetraazacyclododecane (Cyclen) or 3-(1-piperizine).

18. The process of claim 1 wherein the catalyst is 1,4-diazabicyclo[2,2,2]octane (DABCO).

19. The process of claim 1 wherein the catalyst is ethylenediamine, 1,3-diaminopropane (DAP), 3,3'-diamino-N-methyldipropylamine, 1,5,8,12-tetroazadodecane, poly(ethylene amine), 5-benzimidazolecarboxylic acid, 2-dimethylaminopyridine (2-DMAP), 1,8-diazabicyclo[5,4,0]undec-7-ene (DBU), 1,5-diazabycyclo[4,3,0]non-5-ene (DBN) or tetramethylethylenediamine (TMEDA).

* * * * *